United States Patent
Bian et al.

(10) Patent No.: US 9,587,009 B2
(45) Date of Patent: Mar. 7, 2017

(54) MEDIA FOR AFFINITY CHROMATOGRAPHY

(71) Applicant: EMD Millipore Corporation, Billerica, MA (US)

(72) Inventors: Nanying Bian, Lexington, MA (US); Senthil Ramaswamy, Nashua, NH (US); Neil Soice, Camino de la Rosa, CA (US); Chen Wang, Shrewsbury, MA (US); Yuan Wong, Booton, NJ (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 14/325,014

(22) Filed: Jul. 7, 2014

(65) Prior Publication Data

US 2014/0323697 A1    Oct. 30, 2014

Related U.S. Application Data

(62) Division of application No. 12/217,558, filed on Jul. 7, 2008, now Pat. No. 8,772,018.

(60) Provisional application No. 60/958,912, filed on Jul. 10, 2007.

(51) Int. Cl.

| | |
|---|---|
| *G01N 33/552* | (2006.01) |
| *C07K 16/00* | (2006.01) |
| *G01N 33/538* | (2006.01) |
| *B01J 20/10* | (2006.01) |
| *B01J 20/28* | (2006.01) |
| *B01J 20/281* | (2006.01) |
| *B01J 20/283* | (2006.01) |
| *B01J 20/286* | (2006.01) |
| *C03C 11/00* | (2006.01) |
| *C03C 12/00* | (2006.01) |
| *C03C 17/28* | (2006.01) |
| *C07K 1/22* | (2006.01) |

(52) U.S. Cl.
CPC ............ *C07K 16/00* (2013.01); *B01J 20/103* (2013.01); *B01J 20/281* (2013.01); *B01J 20/283* (2013.01); *B01J 20/28004* (2013.01); *B01J 20/286* (2013.01); *B01J 20/28014* (2013.01); *B01J 20/28016* (2013.01); *B01J 20/28026* (2013.01); *B01J 20/28054* (2013.01); *B01J 20/28085* (2013.01); *C03C 11/00* (2013.01); *C03C 12/00* (2013.01); *C03C 17/28* (2013.01); *C07K 1/22* (2013.01); *G01N 33/538* (2013.01); *Y10T 428/2982* (2015.01)

(58) Field of Classification Search
None
See application file for complete search history.

(56) References Cited

U.S. PATENT DOCUMENTS

| | | |
|---|---|---|
| 3,932,557 A | 1/1976 | Matthews |
| 4,210,723 A | 7/1980 | Dorman et al. |
| 4,606,825 A | 8/1986 | Crane et al. |
| 4,772,635 A | 9/1988 | Mitschker et al. |
| 4,973,683 A | 11/1990 | Lindgren |
| 5,084,559 A | 1/1992 | Profy |
| 5,151,350 A | 9/1992 | Colbert et al. |
| 5,250,613 A | 10/1993 | Bergstrom et al. |
| 5,260,373 A | 11/1993 | Profy et al. |
| 5,672,276 A | 9/1997 | Girot et al. |
| 5,874,165 A | 2/1999 | Drumheller |
| 6,399,750 B1 | 6/2002 | Johansson |
| 6,602,990 B1 | 8/2003 | Berg |
| 2005/0143566 A1 | 6/2005 | Hober |
| 2006/0134805 A1 | 6/2006 | Berg et al. |

FOREIGN PATENT DOCUMENTS

| | | |
|---|---|---|
| EP | 1352957 A1 | 10/2003 |
| JP | 59-144460 A | 6/1984 |
| JP | 7-509173 A | 10/1995 |
| WO | 90/09237 A1 | 6/1990 |
| WO | 95/19374 A1 | 7/1995 |
| WO | 2004/074471 A1 | 9/2004 |

OTHER PUBLICATIONS

"Controlled Pore Glass (CPG) Media", Millipore Corporation, Specification Data Sheet, 2006, 2 pages.
Extended European Search Report received for EP Patent Application No. 08160052.0, mailed on Nov. 14, 2008, 10 pages.
Nilsson, et al., "A synthetic IgG-Binding Domain Based on Staphylococcal Protein A", Protein Engineering, vol. 1, No. 2, Jan. 1, 1987, pp. 107-113.
Boyle, et al., "Bacterial Fc Receptors", Nature Biotechnology, vol. 5, 1987, pp. 697-703.
Kemp, et al., "Meeting the Demands in Process-scale Antibody Purification for High Capacity and Throughput", BioPhex, Millipore Technical Publication, 2002, 6 pages.
McCue, et al., "Evaluation of protein-A Chromatography Media", Journal of Chromatography A, vol. 989, No. 1, Mar. 7, 2003, pp. 139-153.
Jungbauer, Alois, "Chromatographic Media for Bioseparation", Journal of Chromatography A, vol. 1065, No. 1, Feb. 11, 2005, pp. 3-12.
Hermanson, et al., "Immobilized Affinity Ligand Techniques", Academic Press, Inc. San Diego, California, 1992, 85 pages.

*Primary Examiner* — Chris L Chin
(74) *Attorney, Agent, or Firm* — EMD Millipore Corporation

(57) ABSTRACT

The invention relates generally to solid supports for chromatography. In specific embodiments the invention provides for solid supports suitable for affinity chromatography along with methods, systems and kits which use the same.

10 Claims, 1 Drawing Sheet

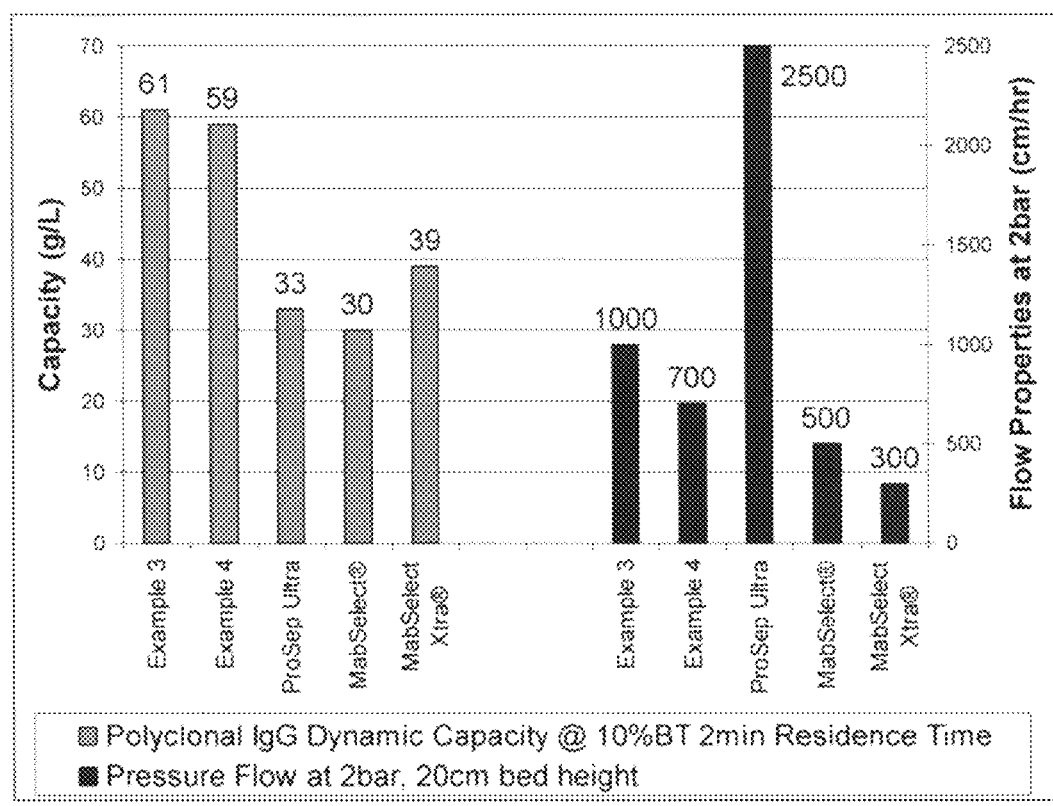

MEDIA FOR AFFINITY CHROMATOGRAPHY

CROSS-REFERENCE RELATED APPLICATIONS

This application is a divisional patent application of U.S. application Ser. No. 12/217,558, filed on Jul. 7, 2008, which claims the benefit of U.S. Provisional Patent Application No. 60/958,912, filed on Jul. 10, 2007, the entire contents of each of which are incorporated by reference herein.

FIELD OF THE INVENTION

The invention relates generally to the field of chromatography. In certain specific embodiments the invention provides a solid support suitable for use in chromatography, e.g., media for affinity chromatography, and methods and kits for using the same, as well as systems for performing a chromatographic process.

BACKGROUND OF THE INVENTION

Affinity chromatography plays an important role in the research, development and production of proteins, including monoclonal antibodies (Mabs). Affinity chromatography media generally comprises a solid support having a bound ligand capable of interacting with a target molecule. Affinity chromatography is useful because the ligands deployed on solid supports, such as beads, are typically selective for the target molecule. This selectivity allows for good yield, as well as fast and economical purification of target molecules. For immunoglobulins (e.g., IgG), including monoclonal antibodies, Protein A is a selective affinity ligand which binds most sub-classes, Boyle, M. D. P., and Reis, K. J., 1987, *Biotechnology*, 5: 697. Protein G is another affinity ligand for IgG. Hermanson, G. T.; Mallia, A. K.; Smith, P. K. *Immobilized Affinity Ligand Techniques*, Academic Press, 1992.

Both Proteins A and G can bind more than one IgG. Once immobilized onto a porous chromatography support such as a resin, membrane or other media, both are useful for purification and commercial production of polyclonal IgG or monoclonal antibodies (Mabs).

Protein A may be isolated in its native form from *Staphylococcus aureus*. Current commercially available Protein A media products such as ProSep vA-HC and n-Protein A Sepharose Fast Flow, use Protein A derived from *S. aureus* (native or n-Protein A). Other commercial affinity media products such as ProSep-rA and MabSelect® employ Protein A recombinantly produced in *E. Coli* (recombinant or r-Protein A). See, e.g., U.S. Pat. No. 5,151,350. Other modified recombinant forms of Protein A have also been described. See. e.g., U.S. Pat. No. 5,084,559; U.S. Pat. No. 6,399,750; US. Patent Publication No. 2005/0143566. Protein A ligands comprising a cysteine residue are also known. U.S. Pat. No. 5,084,559; U.S. Pat. No. 6,399,750. The addition of a cysteine amino acid facilitates ligand coupling to the base matrix or resin. Modifications to the B domain of Protein A have also been-described. US Patent Publication No. 2005/0143566.

There are several parameters that may determine the performance of an affinity chromatography media. Selectivity, effective mass transfer, binding capacity and packed bed permeability all play a role in determining the utility of a media to affect the desired separation. Selectivity of the resin may be driven by the ligand and its properties. Many of the performance characteristics are determined by a combination and interplay of the base matrix properties, type of chemical modification used for ligand attachment and ligand properties.

The base matrix plays a role in determining the pressure-flow characteristics of the media and also determines the "effective pore size" into which the target molecule must diffuse to affect adsorption. For synthetic and natural polymers there is often a relationship between the pore size of the material and the observed rigidity. Typically, the larger the pore size the less rigid a material will become. This is especially true for hydrogels such as agarose. Materials made of unmodified agarose have very poor rigidity where only after chemical modification through crosslinking is a desirable rigidity obtained. U.S. Pat. No. 4,973,683. To attempt to overcome these challenges, further chemical crosslinking has been developed which provides particles with suitable pressure-flow properties. See, e.g., U.S. Pat. No. 6,602,990: GE Healthcare Catalog, 2007. However, these materials are still compressible, which limits operating flowrates, moreover pressures are usually restricted to <2 bar, thus limiting productivity and the operating window available to the end-user. Commercial Protein A affinity media made using agarose or modified agarose include Protein A Sepharose Fast Flow®, r-Protein A Sepharose Fast Flow®, Mabselect® and Mabselect Xtra®. US Patent Publication No. 2006/0134805. Mabselect Xtra® is another version of modified agarose where the pore size, particle size and ligand density have been adjusted for the agarose support. GE Healthcare Catalog, 2007.

Silica based solid supports do not suffer from many of the shortcomings associated with agarose supports. One advantage of using solid supports comprising silica (e.g. glass) or ceramic is that they are inherently incompressible. This allows for the decoupling of the media's pore size from the media's mechanical properties. The media's mechanical properties, e.g. compressibility, largely determine the maximum pressure-flow capabilities. Therefore, silica based solid supports, essentially have pore size and pressure-flow properties that are decoupled whereby one property can be altered without affecting the other. Affinity media based on porous silica, particularly controlled pore glass (CPG), have found commercial utility due to their high capacity and suitable pressure-flow characteristics. McCue. J. et. al., 2003, *Journal of Chromatography*, 989:139. Previously, materials with a pore size of 1000 Å and 700 Å, and particle size of 56 µm to 100 µm have been described. McCue, Justin et. al. Presentation, 225th ACS National Meeting, New Orleans, La., United States, Mar. 23-27, 2003 (2003). Notably the smaller particle size and pore size had the higher capacity, but the capacity improvement was incremental in light of the reduced pressure flow properties. Thus the need for improved capacity remains particularly given the production capacity of large scale preparative methods for protein therapeutics and other biologics.

Currently, the production of monoclonal antibodies is done through the fermentation of mammalian cells in bioreactors on the scale of 10,000-20,000 liters. After clarification, these volumes must be processed through the first chromatography step, which is typically a Protein A column. As fermentation processes and technology improve, the titer concentration in the unprocessed product continually increases, resulting in titers >1 g/L. These higher titer fermentation batches can result in total product protein amounts >20 Kg. Due to the increase in total protein/batch, there is increased demand on the Protein A column binding capacity. Therefore, a need exists to create chromatography materials that have sufficient capacity to bind and purify these large amounts of product protein. Various embodiments of the invention described herein meet this need and others as well.

SUMMARY OF THE INVENTION

In various embodiments the invention provides an improved affinity chromatography media having a combination of higher capacity, e.g., dynamic capacity, and higher packed bed permeability compared to previously described affinity chromatography media, thus providing for improved process throughput which in turn provides for savings in cost and time and other benefits.

In certain embodiments, the invention provides a solid support suitable for performing affinity chromatography comprising a silica particle having a pore size greater than 630 Å and less than 1000 Å and a mean particle size greater than 50 μm, for example greater than 55 μm and less than 70 μm. The particle size may be measured by light scattering means described infra, however, the skilled artisan will recognize that other methods of measuring particle size may be used. The solid support may include particles having distribution of sizes e.g. +/−13 μm of the mean. The solid support may further comprise one or more affinity ligands.

In other embodiments the invention provides an affinity chromatography media, e.g., a solid support comprising silica, and having a dynamic capacity (Qd)≥45 g/L (grams/liter) at 10% breakthrough and a pressure drop of ≤2 bar at a flow rate ≥400 cm/hr for a packed bed height of 20 cm in a column with a diameter ≥3.2 cm. The affinity chromatography media may further comprise one or more affinity ligands.

In still other embodiments the invention provides for a controlled porous glass bead comprising a pore size of 839 Å and a mean particle size of 63 μm and an affinity ligand comprising Protein A or a functional variant thereof linked to the bead.

In still other embodiments the invention provides for a controlled porous glass particle, e.g., a bead, comprising a pore size of 700 Å and a mean particle size of 55 μm with a particle size distribution of +/−13 μm and an affinity ligand. The affinity ligand may comprise Protein A or a functional variant thereof linked to the particle.

In further embodiments the invention provides a method of isolating a target molecule from a mixture comprising: a) contacting the mixture containing the target molecule with an affinity chromatography matrix where the matrix comprises 1) a solid support comprising a silica particle having a pore size greater than 700 Å and less than 1000 Å and a mean particle size greater than 55 μm and less than 70 μm and 2) an affinity ligand having specificity for the target molecule linked to the solid support; and b) eluting the target molecule from the affinity chromatography matrix.

In yet other embodiments the invention provides a method of isolating a target molecule from a mixture comprising: a) contacting the mixture containing the target molecule with an affinity chromatography matrix, wherein the affinity chromatography matrix is contained within a housing, such as a column, and wherein the column packed with the affinity chromatography matrix has a maximum flow rate of at least 400 cm/hr, and wherein the matrix comprises 1) a silica particle and 2) an affinity ligand having specificity for the target molecule, wherein the dynamic capacity of the matrix for the target molecule is at least 45 g/liter at 10% breakthrough; and optionally b) eluting the target molecule from the affinity chromatography matrix.

In yet other embodiments the invention provides a system for isolating a target molecule from a mixture comprising a) an affinity chromatography matrix where the matrix comprises a solid support comprising 1) a silica particle having a pore size greater than 630 Å and less than 1000 Å and a mean particle size greater than 55 μm and less than 70 μm and 2) an affinity ligand having specificity for the target molecule linked to the solid support; and b) a housing for containing the affinity chromatography matrix. The system may optionally include a means to detect elation of the target molecule from the affinity chromatography matrix.

In further embodiment the invention provides a system for isolating a target molecule from a mixture comprising a) an affinity chromatography matrix wherein the affinity chromatography matrix is contained within a housing, such as a column, wherein the column packed with the affinity chromatography matrix has a maximum flow rate of at least 400 cm/hr, and wherein the matrix comprises 1) a silica particle and 2) an affinity ligand having specificity for the target molecule wherein the dynamic capacity of the matrix for the target molecule is at least 45 g/liter. The system may optionally include a means to detect elation of the target molecule from the affinity chromatography matrix.

In other embodiments the invention provides a kit comprising an affinity chromatography matrix comprising a silica particle having a pore size greater than 700 Å and less than 1000 Å and a mean particle size greater than 55 μm and less than 70 μm and at least one container.

In further embodiments the invention provides a kit comprising an affinity chromatography matrix, wherein the affinity chromatography matrix is contained within a housing, such as a column, wherein the column packed with the affinity chromatography matrix has a maximum flow rate of at least 400 cm/hr, and wherein the matrix comprises 1) a silica particle and 2) an affinity ligand having specificity tor the target molecule wherein the dynamic capacity of the matrix for the target molecule is at least 45 g/liter and at least one container.

BRIEF DESCRIPTION OF THE DRAWINGS

FIG. 1 is a graph showing the dynamic capacity and packed bed permeability for an affinity media according to certain embodiments of the invention.

DESCRIPTION OP THE EMBODIMENTS

In some embodiments the invention provides for a chromatography matrix having an improved dynamic capacity, higher flow rate at lower residence times. In certain embodiments the invention provides for an improved affinity chromatography matrix comprised of a silica particle having a defined pore size and defined mean particle size. The improved matrix provides for improved dynamic capacity e.g., greater than 30 g/L for a target molecule, which may be isolated using the matrix, as well as improved maximum flow rate, e.g. greater than 400 cm/hr when the matrix is packed in a column, e.g. at a 20 cm bed height and a pressure of <2 bar. In specific embodiments the invention provides for an affinity chromatography matrix having a dynamic capacity of greater than 49 g/L at 2 minutes residence time with 10% breakthrough. The affinity chromatography matrix, according to the invention, thus provides an improved composition for purifying target molecules, such as proteins, from a mixture, where the target molecule may be present at various concentrations including 1 g/L or greater.

DEFINITIONS

Affinity Ligand, as used herein, refers to a molecule, such as a protein, which specifically binds to a target molecule found in a mixture with greater affinity compared non-target molecules in the mixture. Examples of affinity ligands may include Protein A, Protein G, or functional variants of either, where the target molecule could be an immunoglobulin or Fc region of an immunoglobulin or a molecule comprised of at least a portion of an Fc region of an immunoglobulin. Other examples of suitable affinity ligands may include any known enzyme, where the target molecule would be the enzyme's substrate. Alternatively, the substrate could serve as the affinity ligand where an enzyme specific for the substrate is the target molecule. Still other examples of affinity ligands include antibodies, e.g., monoclonal, polyclonal, where the target molecule comprises an epitope which binds to the variable region of the antibody.

Functional Variant, as used herein refers to a protein having at least one alteration in its native amino acid sequence, but which still maintains at least one function associated with its native sequence. Native sequence includes amino acid sequences naturally occurring in nature. Amino acid alterations may include substitution of one or more amino acids for another, deletion of one or more amino acids, and/or the addition of one or more amino acids or any combination thereof. Truncations are also contemplated as are combinations of additions, deletions and substitutions made in relation to the native sequence. A functional variant may also include a fragment or a domain of a protein. As an example a functional variant could include a full length protein A molecule having at least one altered amino acid, compared to its native sequence; a fragment of a full length Protein A molecule; or a fragment of a full length Protein A molecule having at least one amino acid altered compared to its native sequence provided the variant maintained at least one function associated with the native Protein A. e.g. the ability to specifically bind to an Fc portion of an immunoglobulin. Additional examples of functional variants include a domain, e.g. A, B, C, D, and E domain of protein A, as well as the Z domain or protein Z, a variant of the B domain of Protein A described in the literature (Nilksson et al. (1987) *Protein Engineering* 1(2): 107). The amino acid sequence of the functional variant may be at least 70% identical, at least 75% identical, at feast 80% identical, at least 85% identical, at least 90% identical, at least 95% identical, at least 98% identical to the native amino acid sequence and still maintains at least one function associated with the native sequence.

Protein as used herein includes a polymer of amino acids and does require a specific length. Thus the definition is intended to include proteins, peptides and polypeptides as well as any post expression modifications to the protein including for example glycosylation or pegylation.

Silica as used herein includes silica and any substance which may be derived from silica, including, but not limited to glass.

Affinity Chromatography Media

Affinity Chromatography Media typically comprises a solid support and an affinity ligand coupled to the solid support. Methods of coupling affinity ligands to a solid support are known in the art, see, e.g. PCT Publication WO 90/09237; Hermanson et al. 1992, *Immobilized Affinity Ligand Techniques*, Academic Press; U.S. Pat. Nos. 5,874,165; 3,932,557; 4,772,635; 4,210,723; 5,250,6123; European Patent Application EP 1 352 957 A1, WO 2004/074471. The affinity ligand may be coupled to a solid support by one or more covalent bonds. The covalent bond may be formed by reacting one or more chemical functional groups on the affinity ligand with one or more chemical functional groups on the solid support. Nucleophilic coupling methods may be used with a suitable functional group. Examples of chemical functional groups may include hydroxyl groups, amine groups, thiol groups, carbonyl groups and the like. Alternatively, a functional group on the surface of the solid support may be activated. Suitable groups may include an NHS ester, epoxide or aldehyde. The affinity ligand may be directly coupled to the solid support, or alternatively an intervening linker molecule may be used to couple the affinity ligand to the solid support. A linker may be useful for example to overcome steric hindrance and thus facilitate binding of a target molecule to its affinity ligand. Design of a suitable linker is well within the ordinary skill of the artisan working in the field.

The solid support may be comprised of any suitable material known in the art. Thus the solid support may comprise any porous material. As an example, the porous material may take the form of a membrane, a head, a gel, a cassette, a column, a chip, a slide, a plate or a monolith. Moreover the porous material may comprise a particle having an irregular shape. The porous material may be comprised of an organic or inorganic molecules or a combination of organic and inorganic molecules and may be comprised of one or more functional groups, e.g., an hydroxyl group, suitable for reacting with and/or binding affinity ligands. The porous material may be comprised of a hydrophilic compound, a hydrophobic compound, an oleophobic compound, an oleophilic compound or any combination thereof.

In certain embodiments the solid support (e.g. a particle) may be comprised of a rigid material such as an inorganic molecule. Suitable inorganic molecules may include siliceous material. Examples of suitable siliceous material include particulate glass, controlled porous glass, colloidal silica, wollastonite, silica gel and bentonite. In some embodiments where the solid support is comprised of a controlled porous glass particle, the particle may have a pore size greater than 700 Å. In further embodiments the pore size may be less than 1000 Å. In other embodiments the pore size may have a size ranging from 630 Å to 1175 Å, 720 Å to 950 Å, 782 Å to 932 Å, 800 Å to 932 Å. In certain embodiments the pore size may be 839 Å.

In some embodiments the invention provides for an affinity chromatography matrix comprised of a silica particle with an enhanced binding capacity for a target molecule, (e.g. a dynamic binding capacity) compared to previously described affinity chromatography media comprised of silica particles. The dynamic binding capacity may be measured by monitoring the protein loading to a packed bed of the matrix of interest. Initially, the protein is completely adsorbed and there is no observable protein in the flow-through fractions exiting the column. As the column becomes more saturated with protein (the protein capacity is utilized) a fraction of the initial protein concentration will start to be observed in the flow-through fractions. Eventually, the column will saturate completely and the protein concentration in the flow-through will equal the initial protein concentration entering the column (all of the protein capacity is utilized). In practice, one wants to load the column as much as possible without losing protein in the flow-through. Therefore the dynamic capacity at low levels of protein concentration in the flow-through fractions or "breakthrough" (1-10% of the total protein concentration) provides a representative measurement of the loading capacity in use. Thus comparing different affinity matrices at 1% or 10% breakthrough provides a comparison of the capacity useful to the end user. The chromatography matrix according to the invention thus may have a dynamic binding capacity for a target molecule that is at least 40 g/L, at least 45 g/L, at least 50 g/L, at least 60 g/L In some embodiments the dynamic capacity may be 50 g/L. In other embodiments the dynamic capacity of the chromatography media may range from 40 g/L to 60 g/L, 40 g/L to 50 g/L, 40 g/L to 49 g/L, 42 g/L to 49 g/L, 41 g/L to 47 g/L, 50-60 g/L. In specific embodiments the invention provides for an affinity chromatography media having a dynamic capacity of 49-60 g/L at a 2 minute residence time with a 10% breakthrough. In other embodiments the invention provides an affinity chromatography media having a dynamic capacity of 40-55 g/L at a 2 minute residence time with a 1% breakthrough.

The silica particle may be of any suitable size, depending upon the application. The particle may have a mean particle size greater than 55 µm. The particle may have a mean particle size less than 100 µm. In certain embodiments the mean particle size may range from 55 µm to 90 µm, 60 µm to 80 µm, 60 µm to 70 µm, 55 µm to 67 µm. In a specific embodiment the mean particle size is 63 µm. The particle size distribution may be ±30 µm, ±25 µm, ±20 µm, ±13 µm. In a specific embodiment the invention has a particle size distribution of ±13 µm.

Any affinity ligand may be used in the practice of the invention provided that it is a specific binding partner of a target molecule of interest. The affinity ligand may be a full length protein or a functional variant of a full length protein. The affinity ligand may be a monomer, dimer or multimer of a full length protein or functional variant. Examples of protein ligands may include Protein A, Protein G, the Fc receptor of an antibody, a receptor for a hormone or growth factor. See, e.g., U.S. Pat. Nos. 5,151,350; 5,084,559; 5,260,373; PCT Publication No. WO 95/19374. In other embodiments the protein ligand may be an immunoglobulin, e.g. IgG, IgM, IgA, IgD, IgE or a functional variant thereof.

The amount of affinity ligand coupled to the solid support may depend on the application and the target molecule. Typically the affinity ligand will be couple to the solid support at a density (gram of ligand per liter of solid support that is greater than 1 g/L, 5 g/L, 10 g/L, 15 g/L, 20 g/L. The ligand density may range from 1 g/L to 20 g/L, 5 g/L to 15 g/L, 10 g/L to 15/gL, 12 g/L to 14 g/L.

The affinity ligand may be a naturally occurring molecule or an engineered molecule. In certain embodiments it may be desirable to genetically alter naturally occurring affinity ligands to facilitate either binding to a solid support or orientation of the protein ligand on the solid support or both. Thus, depending on the associative group used, the skilled artisan may engineer charged groups or hydrophobic groups, or both, into the affinity ligand. These changes may be made anywhere within the affinity ligand.

In a specific embodiment the affinity ligand is Protein A, or a functional variant thereof. The Protein A or a functional variant thereof may be recombinantly produced, e.g., in a prokaryotic cell such as *E. coli*. In another embodiment the affinity ligand may be Protein A, obtained from *Staphylococcus aureus*. In some embodiments the affinity ligand may comprise one or more domains, e.g. A, B, C, D, or E domain, of a native Protein A or a functional variant thereof. In other embodiments the affinity ligand may be Protein Z, an altered B domain of Protein A. See, e.g. U.S. Patent Publication No. 2005/0143566. Modifications which improve the performance capability of the protein A ligand are also contemplated. The affinity ligand may be a monomer of Protein A, or a functional variant thereof or a multiuser of Protein A, or a functional variant thereof e.g. comprised of two or more units.

Target molecules may include any molecule which specifically binds to the protein ligand of choice. Where the protein ligand is protein A or protein G the target molecule may include an immunoglobulin of the IgG subclass or a molecule comprised of an Fc portion of an IgG. A specific example of a target molecule may include a monoclonal antibody. Functional variants and fragments of immunoglobulins are also contemplated as target molecules provided that they retain their ability to bind to the affinity ligand of choice. The target molecule may also be a fusion protein, e.g. a molecule comprised of at least a portion of an Fc region of an immunoglobulin such as Embrel® (Amgen, Thousand Oaks, Calif.).

Methods of Purifying a Target Molecule

In certain embodiments the invention provides a method of purifying a target molecule from a mixture. The method may comprise contacting a chromatography matrix, e.g. comprised of an affinity chromatography media with a mixture comprising a target molecule under conditions such that the target molecule preferentially binds to the chromatography matrix and optionally elating the target molecule from the matrix by altering one or more conditions, e.g. by applying an elation buffer. The elation buffer may have for example a pH which differs from the pH of the mixture as it was applied to the matrix, or it may have a higher concentration of salt as compared to the original mixture applied to the matrix. The method may optionally include one or more wash steps. The wash steps may be performed for example after the target molecule has bound to the matrix, hut before the target molecule has been eluted from the matrix. Additional wash steps may optionally be performed after the elation of the target molecule, e.g., to clean the matrix of residually bound material. The cleaning wash buffer may have an acidic pH or alternatively a basic pH.

The affinity chromatography matrix of the invention may be used in any known method of purifying a target molecule from a mixture. Thus the matrix may be used in a batch formulation wherein the matrix is added directly to a mixture containing the target molecule. The matrix may also be packed into a column such that the mixture containing the target molecule is passed through the column containing the matrix.

The method may provide for an increased maximum flow rate (e.g. over a column comprising an affinity chromatography matrix), compared to other known affinity chromatography methods. By adjusting the particle size and the pore size, target molecule binding and flow rate may both be improved thus increasing both yield and efficiency. In certain embodiments the invention provides a method of isolating a target protein from a mixture wherein the mixture contacts the affinity chromatography matrix contained in a housing, e.g., a column, wherein the mixture flows through the column containing the media at a maximum flow rate of at least 400 cm/hr, at least 500 cm/hr, at least 600 cm/hr, at least 700 cm/hr, at least 800 cm/hr, at least 900 cm/hr. In some embodiments the maximum flow rate may range from 400 cm/hr-1000 cm/hr, 400 cm/hr-900 cm/hr, 500 cm/hr-900 cm/hr, 600 cm/hr-900 cm/hr, 700 cm/hr-900 cm/hr, 600 cm/hr-800 cm/hr, 700 cm/hr-800 cm/hr.

The flow rate may be determined by the bed height of the affinity chromatography media. For example bed heights may range from 10-30 cm, with flowrates ranging from 100-700 cm/hr. The matrices permeability may limit the flow-rate that can be used. For example, agarose media typically cannot be used at flowrates >500 cm/hr at 20 cm bed height. Controlled pore glass media may be run at 1000-2500 cm/hr at 20 cm/bed height, and may be configured at 30 cm bed height and still yield flowrates >500 cm/hr. in many cases the flowrate limits the productivity of the media filled column, which can greatly affect the economics and throughput of protein purification processes.

Currently, one factor creating these flowrate limitations is the equipment used for protein purification. Most systems operate at relatively low pressures, <3 bar, with an acceptable range typically less than 2 bar. Though higher pressures might broaden the flowrate window for agarose and other limited media, the incompressible controlled pore glass can better utilize increased pressure, while compressible media such as agarose may see only incremental flowrate increases due to rigidity limitations.

Chromatography Systems

In some embodiments the invention provides a system for isolating a target molecule from a mixture. The system may include an affinity chromatography matrix comprising a silica particle. The system may also include a housing suitable for containing the affinity chromatography matrix including one or more columns suitable for packing with a chromatography matrix. The columns may be comprised of any suitable material including metal or plastic. The system may include one or more pumps to facilitate flow of the mixture over the chromatography matrix. Suitable pumps include peristaltic pumps, pulsed pumps and/or positive displacement pumps. The system may take the form of a high pressure liquid chromatography system (HPLC), medium pressure liquid chromatography system (MPLC) or a low pressure liquid chromatography system (LPLC). The system may include one or more means to detect the contents of an eluant from the chromatography media. The detector may be a light based detector which relies on multi-wavelength detection or single wavelength detection. Suitable detectors include a spectrophotometer capable of detecting visible wavelengths of light, a UV absorption detector, a fluorescence detector. The detector may be a light scattering detector which relies on a laser source or an electrochemical detector which responds to substances that are either oxidizable or reducible and the electrical output is an electron, flow generated by a reaction that takes place at the surface of the electrodes. The system may also include one or more printers for providing chromatograms of the elated material from the chromatography media. The system may also include one or more personal computers. The personal computer may be suitable for recording data, such as the absorbance or fluorescence of an elation fraction. Additionally the computer may be equipped with suitable software to calculate the concentration of a target molecule in an elution fraction. The computer may also be used to automate the process of performing affinity chromatography such that samples are applied to the chromatography matrix, the matrix is washed with one or more suitable buffers and the target molecule is optionally elated off of the matrix with a suitable elution buffer. The system may also provide for a computer controlled automated cleaning step whereby the chromatography media is regenerated after use with a suitable cleaning reagent.

Kits

The invention also provides for a kit comprising a chromatography solid support and at least one container. The chromatography solid support may be an affinity chromatography solid support comprising a silica particle having a defined pore size and a defined particle size. The silica particle may include any of the particle attributes described infra. The kit may optionally include one or more affinity ligands. The solid supports may be provided with the affinity ligand coupled to the solid support, or alternatively the affinity ligand may be provided separately from the solid support. The kit may optionally include a housing to contain the solid supports such as one or more columns, which may be packed with the solid support. The kit may also optionally include one or more reagents. Where the solid support and the affinity ligand are provided separately, the reagents may include reagents for coupling the affinity ligand to the solid support. The coupling reagent may include for example a reagent which reacts with a hydroxyl functionality. Other optional reagents may include wash buffers for example, suitable for removing non-specifically bound molecules, e.g. phosphate buffered saline or water and elution buffers suitable for eluting a target molecule from the affinity chromatography media, e.g. a solution having an acidic pH. The kit may optionally include one or more controls. Controls may include target molecules such as immunoglobulins, and/or affinity ligands, such as protein A, protein G, or a functional variant of either. The kit may optionally include instructions. The instructions may provide guidance concerning one or more of the following: linking affinity ligands to the solid support: packing columns with affinity chromatography media comprising silica solid supports, isolating a target molecule using affinity chromatography media comprising silica solid supports; cleaning the chromatography media after use; equilibrating the chromatography media before use.

EXAMPLES

Example 1

Silica Affinity Matrix with Different Pore Sizes

Controlled pore glass beads (50 mL each, mean particle size of 63 µm) with pore sizes ranging from 500 Å to 1200 Å were functionalized with Protein A according to the method for coupling Protein A to a solid support described in WO 90/09237. A Protein A ligand density of 12-14 g/L was attained. After ligand coupling, the samples were washed three cycles with 150 mL volume of each (in order); 0.1M Tris with 0.15M NaCl pH 8 followed by 0.05M Acetic Acid. Afterwards, the samples were equilibrated and stored in PBS w/azide. The samples were tested for dynamic IgG binding capacity at 2 min flow residence time as described in Example 5 below. The properties for the affinity matrix of different pore sizes are shown in Table 1.

TABLE 1

Properties of Silica Affinity matrix with different pore sizes

| CPG Pore Size | $Qd_{10\% BT}$ (g/L) |
|---|---|
| 489 Å | 22 |
| 629 Å | 50 |
| 700 Å | 54 |
| 782 Å | 60 |
| 839 Å | 61 |
| 889 Å | 60 |
| 932 Å | 58 |
| 1034 Å | 45 |
| 1175 Å | 46 |

Example 2

Silica Affinity Matrix with Different Particle Sizes and Particle Size Distributions Controlled pore glass beads (700 Å pore size, 50 mL each) with the described mean particle size (measured by light scattering) were functionalized with Protein A according to the method for coupling Protein A to a solid support described in WO 90/09237. A Protein A ligand density of 12-14 g/L was attained. After ligand coupling, the samples were washed three cycles with 150 mL volume of each (in order): 0.1M Tris with 0.15M NaCl, pH 8 followed by 0.05M Acetic Acid. Afterwards, the samples were equilibrated and stored in PBS w/azide. The samples were tested for dynamic IgG binding capacity at 2 mm flow residence time as described in Example 5 below. The properties for the affinity matrix of different pore sizes are shown in Table 2.

TABLE 2

Properties of Silica Affinity matrix with different particle size distributions

| Example | Mean Particle Size (μm) | $Qd_{10\% BT}$ (g/L) |
| --- | --- | --- |
| 2.1 | 67 | 49 |
| 2.2 | 65 | 49 |
| 2.3 | 64 | 51 |
| 2.4 | 62 | 52 |
| 2.5 | 61 | 53 |
| 2.6 | 55 | 59 |

Example 3

Silica Affinity Matrix Properties with 65 μm Particle Size and Particle Size Distribution and 840 Å Pore Size Controlled pore glass beads (839 Å pore size, 63 μm mean particle size, 50 mL volume) was functionalized with Protein A according to the method for coupling Protein A to a solid support described in WO 90/09237. A Protein A ligand density of 13 g/L was attained. After ligand coupling, the samples were washed three cycles with 150 mL volume of each (in order): 0.1M Tris with 0.15M NaCl, pH 8 followed by 0.05M Acetic Acid. Afterwards, the samples were equilibrated and stored in PBS w/azide. The samples were tested for dynamic IgG binding capacity as described in Example 5. The properties for this affinity matrix is shown in FIG. 1.

Example 4

Silica Affinity Matrix Properties with 55 μm Particle Size and Particle Size Distribution and 700 Å Pore Size Controlled pore glass beads (700 Å pore size, 55±13 μm mean particle size, 50 mL volume) was functional teed with Protein A according to the method for coupling Protein A to a solid support described in WO 90/09237. A Protein A ligand density of 13 g/L was attained. After ligand coupling, the samples were washed with 150 mL volume of each (in order): 0.1M Tris Buffer, 0.15M NaCl, pH 8, 0.05M Acetic Acid, PBS w/azide. The samples were tested for dynamic IgG binding capacity as described in Example 5. The properties for this affinity media is shown in FIG. 1.

Example 5

Determining IgG Dynamic Capacity

The Protein A media were packed into omnifit columns (0.66 cm diameter, 7 cm bed height) (Bio Chem Valve. Inc. Boontown, N.J.) and tested for dynamic binding capacity of polyclonal human Immunoglobulin (IgG). The columns were equilibrated with PBS buffer (pH 7.4) and the protein (2 g/L) was loaded onto the column with this same buffer under equivalent flow rate conditions. The capacity at 10% breakthrough was used to compare the different media.

Example 6

Determining the Mean Particle Size and Particle Size Distribution of the Affinity Matrix Controlled pore glass particle size distribution was determined using a laser-diffraction Malvern Mastersizer S (633 nm) (Worcestershire, UK). Rotator speed was set at 2500. CPG sample of interest was suspended in Milli-Q water until it reached obscuration between 15-20% for optimum detection. Mean pore diameter generated using the Mie theory is reported.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A controlled porous glass bead comprising a pore size of about 839 Å; a mean particle size of 63 μm and an affinity ligand comprising Protein A linked to the bead, the affinity ligand having an affinity ligand density from 12 g/L to 14 g/L.

2. A controlled porous glass bead comprising a pore size of about 700 Å; a mean particle size of 55 μm±13 μm and an affinity ligand comprising Protein A linked to the bead, the affinity ligand having an affinity ligand density from 12 g/L to 14 g/L.

3. A method of isolating a target molecule comprising: a) contacting a mixture containing the target molecule with an affinity chromatography matrix where the matrix comprises 1) a solid support comprising a silica particle having a pore size greater than 630 Å and less than 1000 Å and a mean particle size greater than 55 μm and less than 70 μm and 2) an affinity ligand having specificity for the target molecule linked to the solid support, the affinity ligand having an affinity ligand density from 12 g/L to 14 g/L; and optionally
b) eluting the target molecule from the affinity chromatography matrix.

4. The method of claim 3, wherein the affinity chromatography matrix is contained in a housing and the contacting step comprises running the mixture containing the target molecule over the affinity chromatography matrix at a maximum flow rate ranging from 600 cm/hour to 900 cm/hour.

5. The method of claim 3, wherein the target molecule comprises at least a portion of an immunoglobulin.

6. The method of claim 3, wherein the target molecule comprises a monoclonal antibody or a polyclonal antibody.

7. The method of claim 3, wherein the target molecule comprises at least a portion of an Fc region of an immunoglobulin.

8. The method of claim 3, wherein the affinity ligand comprises Protein A.

9. The method of claim 3, wherein the target molecule is eluted from the affinity chromatography matrix with a buffer having an acidic pH.

10. The method of claim 3, wherein the affinity chromatography matrix has a dynamic binding capacity for the target molecule of at least 45 g/liter.

* * * * *